United States Patent [19]

Neumann

[11] 4,086,353
[45] Apr. 25, 1978

[54] CERTAIN AZOLINYLAMINO (AZOLIDINYLIMINO) INDAZOLES

[75] Inventor: Peter Neumann, Bern, Switzerland

[73] Assignee: Sandoz Ltd., Basel, Switzerland

[21] Appl. No.: 745,303

[22] Filed: Nov. 26, 1976

[30] Foreign Application Priority Data

| Dec. 3, 1975 | Switzerland | 15716/75 |
| Jul. 20, 1976 | Switzerland | 9279/76 |
| Dec. 22, 1975 | Switzerland | 16645/75 |
| Jul. 21, 1976 | Switzerland | 9312/76 |

[51] Int. Cl.² .............. C07D 417/12; A61K 31/425; A61K 31/42; C07D 413/12
[52] U.S. Cl. ............. 424/272; 260/306.7 T; 260/307 F; 260/307 FA; 424/270
[58] Field of Search ............. 260/306.7 T, 307 FA, 260/307 F; 424/270, 272

[56] References Cited

U.S. PATENT DOCUMENTS 3,759,903  9/1973  Haugwitz et al. .......... 260/306.7 T

*Primary Examiner*—Richard J. Gallagher
*Attorney, Agent, or Firm*—Gerald D. Sharkin; Robert S. Honor; Thomas O. McGovern

[57] ABSTRACT

The present invention provides compounds of formula I,

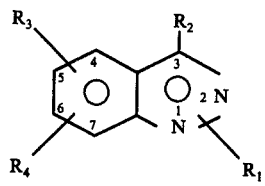

wherein
$R_1$ is hydrogen or alkyl of 1 to 4 carbon atoms in position 1 or 2 of the indazole nucleus,
$R_2$ is hydrogen, halogen, trifluoromethyl, hydroxy or alkyl, alkylthio or alkoxy of 1 to 4 carbon atoms, or a group of formula II,

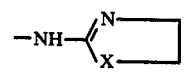

wherein
X is oxygen or sulphur,
$R_3$ is hydrogen, halogen, trifluoromethyl, hydroxy or alkyl, alkylthio or alkoxy of 1 to 4 carbon atoms, and
$R_4$ is hydrogen or a group of formula II, as defined above, with the proviso that one of $R_2$ and $R_4$ is a group of formula II and the other is other than a group of formula II, useful as myotonolytics and anti-hypertensives.

105 Claims, No Drawings

CERTAIN AZOLINYLAMINO (AZOLIDINYLIMINO) INDAZOLES

IMPROVEMENTS IN OR RELATING TO ORGANIC COMPOUNDS

The present invention concerns indazole derivatives. The present invention provides compounds of formula I, <pre>
      R_3     R_2
        \\ 4   /
         5   3
        /   \\   2 N
       6     \\ /
        \\ 7   N
         R_4    R_1
</pre>
I wherein $R_1$ is hydrogen or alkyl of 1 to 4 carbon atoms, in position 1 or 2 of the indazole nucleus, $R_2$ is hydrogen, halogen, trifluoromethyl, hydroxy or alkyl, alkylthio or alkoxy of 1 to 4 carbon atoms, or a group of formula II, $$-NH-C\underset{X}{\overset{N}{\diagup\diagdown}}$$  II wherein X is oxygen or sulphur, $R_3$ is hydrogen, halogen, trifluoromethyl, hydroxy or alkyl, alkylthio or alkoxy of 1 to 4 carbon atoms, and $R_4$ is hydrogen or a group of formula II, as defined above, with the proviso that one of $R_2$ and $R_4$ is a group of formula II and the other of $R_2$ and $R_4$ is other than a group of formula II.

The group of formula II in a compound of formula I may exist in the tautomeric form of formula IIa, $$-N=C\underset{X}{\overset{\overset{H}{N}}{\diagup\diagdown}}$$  IIa For the sake of simplicity the groups of formulae II and IIa are regarded hereinafter as a group of formula II.

Halogen means fluorine, chlorine, bromine or iodine, preferably chlorine or bromine. Alkyl, alkoxy and alkylthio preferably have 1 or 2 carbon atoms. Preferably two of the substituents $R_1$, $R_2$, $R_3$ and $R_4$ are hydrogen. $R_1$ is preferably in position 1. $R_2$ is preferably hydrogen. $R_3$ is preferably hydrogen, chlorine or methyl. The group of formula II is preferably $R_4$.

The present invention also provides a process for the production of a compound of formula I, as defined above, which comprises cyclizing a compound of formula III, <pre>
      R_3'    R_2'
        \\    /
         \\  /
          \\/
          /\\    N
         /  \\  /
        /    \\/
       R_4'    N
               \\
                R_1
</pre>
III wherein $R_1$ and $R_3$ are as defined above, $R_2'$ is hydrogen, halogen, alkyl or alkylthio or alkoxy of 1 to 4 carbon atoms, trifluoromethyl, hydroxy or a group of formula IV, $$-N=\overset{\overset{SR_5}{|}}{C}-NH-CH_2-CH_2OH$$  IV wherein $R_5$ is hydrogen or alkyl of 1 to 4 carbon atoms, or a tautomeric form thereof, and $R_4'$ is hydrogen or a group of formula IV or a tautomeric form thereof, with the provisos that (a) one of $R_2'$ and $R_4'$ is a group of formula IV or a tautomeric form thereof and the other of $R_2'$ and $R_4'$ is other than a group of formula IV or a tautomeric form thereof, and (b) when X is sulphur in the compound of formula I, $R_5$ is hydrogen.

The reaction may be effected in conventional manner for cyclization reactions with analogous compounds.

The reaction may be effected in an inert solvent, e.g. methanol, ethanol, water or dimethylformamide. Suitable temperatures range between 20° and 150° C, preferably between 60° and 110° C, e.g. reflux temperatures.

For the production of a compound of formula I, wherein X is oxygen, conveniently a base such as an alkali hydroxide, e.g. sodium or potassium hydroxide, and alkali earth metal hydroxide, or an alkali metal alcoholate, e.g. sodium or potassium methylate or ethylate is present. Alternatively or additionally, mercury acetate or lead acetate is conveniently present.

For the production of a compound of formula I, wherein X is sulphur, conveniently an acid, e.g. hydrochloric acid, sulphuric acid or methane-sulphonic acid, is present.

The compounds of formula I may be isolated and purified in conventional manner. Free base forms of the compounds may be converted into acid addition salt form in conventional manner and vice versa. Suitable acids for salt formation include inorganic acids such as hydrochloric acid, and organic acids such as acetic acid and maleic acid.

The starting materials of formula III, wherein $R_5$ is hydrogen, may be obtained by reacting the corresponding amino-indazole with thiophosgene, and reacting the resultant isothiocyanato-indazole with ethanolamine. Starting materials of formula III, wherein $R_5$ is alkyl, may be produced by alkylating the corresponding compounds wherein $R_5$ is hydrogen.

Insofar the production of any starting material is not particularly described, these compounds are known, or may be produced and purified in accordance with known processes or in a manner analogous to known processes or to processes described herein.

In the following Examples all temperatures are in degrees Centigrade and are uncorrected.

EXAMPLE 1:
1-Methyl-7-(2-oxazolin-2-ylamino)-1H-indazole 10.6 g of N-(2-hydroxyethyl)-N'-(1-methyl-1H-indazolyl-7)-thiourea are dissolved in 1200 ml of hot ethanol (50°) and treated with 14 g of mercury (II) acetate. The mixture is boiled for 10 minutes. The mixture is filtered whilst hot to remove a black precipitate. The filtrate is evaporated to 400 ml, filtered through active charcoal, and treated at 90° with a filtered solution of 6.1 g naphthalene-1,5-disulphonic acid in 100 ml of alcohol. The title compound crystallizes out slowly as the bis[base]naphthalene-1,5-disulphonate; M.Pt. 266° – 268°.

The starting material is prepared as follows: 3 g of 1-methyl-7-isothiocyanato-indazole is added to a stirred mixture of 2 ml of ethanolamine and 100 ml of ether, thus forming a white precipitate. After 2 hours the precipitate is filtered off and washed with ether to yield the starting material; M.Pt. 207° – 209°.

EXAMPLE 2:
1-Methyl-(2-oxazolin-2-yl-amino)-1H-indazole

A suspension of 12 g of N-(2-hydroxyethyl)-N'-(1-methyl-1H-indazolyl-4)-thiourea in 600 ml of ethanol is treated at 70° with a solution of 2.7 g of sodium in 70 ml of ethanol. The resultant clear solution is stirred, and, when still at 70° C, has added to it portionwise 16 g of mercury (II) acetate over 1 minute. The mixture is boiled for 5 minutes, and then filtered. The filtrate is evaporated to dryness and the residue is partitioned between 70 ml 1N hydrochloric acid and 50 ml methylene chloride. The aqueous phase is treated with active charcoal, filtered and made alkaline with concentrated aqueous ammonia. The resultant precipitate is filtered and crystallized from ethyl acetate to yield the title compound in free base form having a M.Pt. 163° – 166°.

EXAMPLE 3:
4-Chloro-5-(2-oxazolin-2-ylamino)-1H-indazole

A mixture of 5.4 g of N-(2-hydroxyethyl)-N'-(4-chloro-1H-indazolyl-5)-thiourea, 100 ml of ethanol, and 4.3 g of methyl iodide is boiled for 15 minutes. Excess methyl iodide is removed by evaporation. The resultant S-methyl-N-(2-hydroxyethyl)-N'-(4-chloro-1H-indazolyl-5)-isothiouronium iodide is treated with a solution of 1.2 g of sodium in 40 ml of ethanol, and boiled for a further 30 minutes. The mixture is filtered whilst hot. The filtrate is treated with 2.5 g of ammonium chloride and evaporated to dryness. The residue is tretated with 150 ml of water and filtered. The resultant precipitate is dissolved in 20 ml of hydrochloric acid and extracted twice with 20 ml of methylene chloride. The aqueous phase is treated with active charcoal, filtered and made alkaline with concentrated aqueous amonia to yield a colourless precipitate. This precipitate is crystallized from isopropanol to yield the title compound in free base form; M.Pt. 223° – 225°.

The following compounds of formula I, wherein X is a 2-oxazolin-2-ylamino group, may be made in analogous manner to that disclosed in Examples 1, 2 and 3.

| Example | $R_1$ | $R_2$ | $R_3$ | $R_4$ | M.Pt. |
|---|---|---|---|---|---|
| 4 | H | X | H | H | 235° – 238° |
| 5 | H | H | H | 4-x | 217° |
| 6 | 2-CH$_3$ | H | H | 4-x | 221° – 224° |
| 7 | H | Cl | H | 4-x | 265° – 268° |
| 8 | 1-CH$_3$ | Cl | H | 4-x | 156° – 158° |
| 9 | 2-CH$_3$ | Cl | H | 4-x | 194° – 196° |
| 10 | H | H | 5-CH$_3$ | 4-x | 222° – 225° |
| 11 | 1-CH$_3$ | H | 5-CH$_3$ | 4-x | 189° – 191° |
| 12 | 2-CH$_3$ | H | 5-CH$_3$ | 4-x | 197° – 199° |
| 13 | H | H | 5-Cl | 4-x | |
| 14 | 1-CH$_3$ | H | 5-Cl | 4-x | |
| 15 | 2-CH$_3$ | H | 5-Cl | 4-x | |
| 16 | H | H | H | 5-x | 185° – 188° |
| 17 | 1-CH$_3$ | H | H | 5-x | 178° – 180° |
| 18 | 2-CH$_3$ | H | H | 5-x | 198° – 202° |
| 19 | H | H | 4-CH$_3$ | 5-x | 210° – 214° |
| 20 | 1-CH$_3$ | H | 4-CH$_3$ | 5-x | 173° – 174° |
| 21 | 2-CH$_3$ | H | 4-CH$_3$ | 5-x | |
| 22 | 1-CH$_3$ | H | 4-Cl | 5-x | 158° – 160° |
| 23 | 2-CH$_3$ | H | 4-Cl | 5-x | 211° – 218° |
| 24 | H | H | 6-CH$_3$ | 5-x | 225° – 227° |
| 25 | 1-CH$_3$ | H | 6-CH$_3$ | 5-x | |
| 26 | 2-CH$_3$ | H | 6-CH$_3$ | 5-x | |
| 27 | H | H | 6-Cl | 5-x | 218° – 221° |
| 28 | 1-CH$_3$ | H | 6-Cl | 5-x | 199° – 204° |
| 29 | 2-CH$_3$ | H | 6-Cl | 5-x | 198° – 201° |
| 30 | H | H | H | 6-x | 197° – 199° |
| 31 | 1-CH$_3$ | H | H | 6-x | 177° 179° |
| 32 | 2-CH$_3$ | H | H | 6-x | 207° – 212° |
| 33 | H | H | 5-CH$_3$ | 6-x | |
| 34 | 1-CH$_3$ | H | 5-CH$_3$ | 6-x | |
| 34a | 2-CH$_3$ | H | 5-CH$_3$ | 6-x | |
| 35 | H | H | 5-Cl | 6-x | 212° – 214° |
| 36 | 1-CH$_3$ | H | 5-Cl | 6-x | 183° – 186° |
| 37 | 2-CH$_3$ | H | 5-Cl | 6-x | 204° – 207° |
| 38 | H | H | H | 7-x | 196° – 198° |
| 39 | 2-CH$_3$ | H | H | 7-x | 164° – 166° |
| 40 | H | H | 5-CH$_3$ | 7-x | 204° – 206° |
| 41 | H | H | 6-CH$_3$ | 7-x | 224° – 227° |
| 42 | 1-CH$_3$ | H | 6-CH$_3$ | 7-x | 148° – 152° |
| 43 | H | H | 6-Cl | 7-x | 229° – 231° |
| 44 | 1-CH$_3$ | H | 6-Cl | 7-x | |
| 45 | 2-CH$_3$ | H | 6-Cl | 7-x | |

EXAMPLE 46:
6-Methyl-5-(2-thiazolin-2-ylamino)-1H-indazole 4 g of N-(2-hyroxyethyl)-N'-(6-methyl-1H-indazolyl-5)-thiourea in 10 ml of concentrated hydrochloric acid are heated for 3 minutes on a steam bath. The solution is treated with 30 ml hot water, treated with active charcoal and filtered. The colourless filtrate is made alkaline with concentrated aqueous sodium hydroxide solution. The resultant precipitate is filtered off and crystallized from methanol/ethyl acetate to yield the title compound in free base form; M.Pt. 218° – 221°.

The following compounds of formula I, wherein x is a 2-thiazolin-2-ylamino group, may be made in analogous manner to that disclosed in Example 46.

| Example | $R_1$ | $R_2$ | $R_3$ | $R_4$ | M.Pt. |
|---|---|---|---|---|---|
| 47 | H | X | H | H | 222°–224° |
| 48 | H | H | H | 4-x | 276°–278° |
| 49 | 1-CH$_3$ | H | H | 4-x | 183°–184° |
| 50 | 2-CH$_3$ | H | H | 4-x | 160°–162° |
| 51 | H | Cl | H | 4-x | 227°–229° |
| 52 | 1-CH$_3$ | Cl | H | 4-x | 188°–190° |
| 53 | H | H | 5-CH$_3$ | 4-x | 274°–277° (maleate 165–168) |
| 54 | 1-CH$_3$ | H | 5-CH$_3$ | 4-x | 138°–140° |
| 55 | 2-CH$_3$ | H | 5-CH$_3$ | 4-x | 78°–79° (maleate 175–177) |
| 56 | H | H | 5-Cl | 4-x | |
| 57 | 1-CH$_3$ | H | 5-Cl | 4-x | |
| 58 | H | H | H | 5-x | 197°–199° |
| 59 | 1-CH$_3$ | H | H | 5-x | 170°–171° |
| 60 | 2-CH$_3$ | H | H | 5-x | 156°–157° |
| 61 | H | H | 4-CH$_3$ | 5-x | 206°–209° (hydrochloride 260–270) |
| 62 | 1-CH$_3$ | H | 4-CH$_3$ | 5-x | 189°–191° |
| 63 | 2-CH$_3$ | H | 4-CH$_3$ | 5-x | 194°–196° (maleate 158–162) |
| 64 | H | H | 4-Cl | 5-x | 230°–236° hydrochloride |
| 65 | 1-CH$_3$ | H | 4-Cl | 5-x | 200°–201° |
| 66 | 2-CH$_3$ | H | 4-Cl | 5-x | 216°–218° |
| 67 | 1-CH$_3$ | H | 6-CH$_3$ | 5-x | |
| 68 | H | H | 6-Cl | 5-x | 177°–178° maleate |
| 69 | 1-CH$_3$ | H | 6-Cl | 5-x | 231°–233° |
| 70 | 2-CH$_3$ | H | 6-Cl | 5-x | 207°–209° |
| 71 | H | H | H | 6-x | 182°–184° |
| 72 | 1-CH$_3$ | H | H | 6-x | |
| 73 | 2-CH$_3$ | H | H | 6-x | 240°–250° hydrochloride |
| 74 | H | H | 5-CH$_3$ | 6-x | |
| 75 | 1-CH$_3$ | H | 5-CH$_3$ | 6-x | |
| 75a | 2-CH$_3$ | H | 5-CH$_3$ | 6-x | |
| 76 | H | H | 5-Cl | 6-x | 254°–257° |
| 77 | 1-CH$_3$ | H | 5-Cl | 6-x | 213°–215° |

-continued

| Example | $R_1$ | $R_2$ | $R_3$ | $R_4$ | M.Pt. |
|---|---|---|---|---|---|
| 78 | H | H | H | 7-x | 206°–208° |
| 79 | 1-$CH_3$ | H | H | 7-x | 135° |
| 80 | 2-$CH_3$ | H | H | 7-x | 176°–178° |
| 81 | 1-$CH_3$ | Cl | H | 7-x | 128°–130° |
| 82 | H | H | 6-$CH_3$ | 7-x | 243°–246° |
| 83 | 1-$CH_3$ | H | 6-$CH_3$ | 7-x | 110°–115° |
| 84 | H | H | 6-Cl | 7-x | 233°–235° |
| 85 | 1-$CH_3$ | H | 6-Cl | 7-x | |
| 86 | 2-$CH_3$ | H | 6-Cl | 7-x | |
| 87 | H | $C_2H_5$ | 7-$SC_2H_5$ | 4-x | |
| 88 | H | $SC_2H_5$ | 7-$SC_2H_5$ | 4-x | |
| 89 | H | $OC_2H_5$ | 7-$OC_2H_5$ | 4-x | |
| 90 | H | $CF_3$ | 7-$CF_3$ | 4-x | |
| 91 | H | OH | 7-OH | 4-x | |

The compounds of formula I have not been described in the literature.

The compounds of formula I are useful because they possess pharmacological activity in animals. In particular, the compounds of formula I are useful as anti-hypertensive agents, as indicated by a lowering of blood pressure of experimentally induced hypertonia in rats on oral administration at a dose of 0.01 to 0.5 mg/kg animal body weight of the compounds. [Method of F. Gross, P. Lustallot and F. Sulser, Arch. exper. Path. Phamakol. 229, 381–388 (1956)].

For the above-mentioned use the dosage will, of course, vary depending on the compound employed, mode of administration and therapy desired. However, in general, satisfactory results are obtained when administered at a daily dosage of from 0.007 mg to about 0.5 mg per kg animal body weight, conveniently given in divided doses 2 to 4 times a day or in sustained release form. For the larger mammal, the total daily dosage is in the range from about 0.5 to about 30 mg, and dosage forms suitable for oral administration comprise from about 0.1 mg to about 15 mg of the compounds admixed with a solid or liquid pharmaceutical carrier or diluent.

Additionally, the compounds are useful as myotonolytics, e.g. for the treatment of spastic conditions, and as muscle relaxants, as indicated in standard tests; e.g. in rabbits on i.v. administration of from 0.001 to 0.1 mg/kg amimal body weight a significant muscle-relaxing effect is observed in accordance with the method of Teschendorf et al, Arch. Exp. Pharmacol. 226, 467–468 (1970), and an inhibition of the rigor induced by Thalamonal is observed in rats on i.v. administration of from about 0.001 to about 5 mg/kg.

For the above-mentioned use the dosage will, of course, vary depending on the compound employed, mode of administration and therapy desired. However, in general, satisfactory results are obtained when administered at a daily dosage of from 0.0002 mg to about 1 mg per kg animal body weight, conveniently given in divided doses 2 to times a day or in sustained release form. For the larger mammal, the total daily dosage is in the range from about 0.01 to about 10 or 50 mg, e.g. 0.1 and 6, preferably between 0.15 and 3 mg. Dosage forms suitable for oral administration conveniently comprise from about 0.0025 mg to about 25 mg of the compounds admixed with a solid or liquid pharmaceutical carrier or diluent.

The compounds of Examples 1, 2 and 3 exhibit especially interesting activity.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be in the form of, for example, a solution or a tablet.

I claim:

1. A compound of formula I,

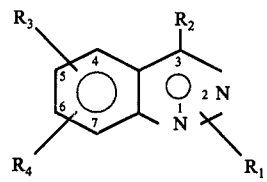

wherein
$R_1$ is hydrogen, or alkyl of 1 to 4 carbon atoms, in position 1 or 2 of the indazole nucleus,
$R_2$ is hydrogen, halogen, trifluoromethyl, hydroxy or alkyl, alkylthio or alkoxy of 1 to 4 carbon atoms, or a group of formula II,

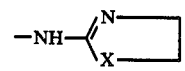

wherein X is oxygen or sulphur, $R_3$ is hydrogen, halogen, trifluoromethyl, hydroxy or alkyl, alkylthio or alkoxy of 1 to 4 carbon atoms, and
$R_4$ is hydrogen or a group of formula II, as defined above,
with the proviso that one of $R_2$ and $R_4$ is a group of formula II and the other of $R_2$ and $R_4$ is other than a group of formula II,
in free base form or in pharmaceutically acceptable acid addition salt form.

2. A pharmaceutical composition useful as an antihypertensive or a myotonolytic comprising an antihypertensive or a myotonolytic effective amount of a compound of claim 1 in association with a pharmaceutical carrier or diluent.

3. A method of treating spastic conditions, or relaxing muscles, or hypertonia which comprises administering a myotonolytic or antihypertensive effective amount of a compound of claim 1 to an mammal in need of such treatment.

4. A compound of claim 1, wherein X is O.

5. A compound of claim 1, wherein X is S.

6. A pharmaceutical composition according to claim 2 in which the compound is 1-methyl-4-(2-oxazolin-2-yl-amino)-1H-indazole.

7. A method according to claim 3 in which the compound is 1-methyl-4-(2-oxazolin-2-yl-amino)-1H-indazole.

8. A compound of claim 4, which is 1-methyl-4-(2-oxazolin-2-yl-amino)-1H-indazole.

9. A compound of claim 4, wherein the 2-oxazolin-2-yl-amino group is in the 3 position of the indazole nucleus.

10. The compound of claim 9, wherein $R_1$, $R_3$ and $R_4$ are all hydrogen.

11. A compound of claim 4, wherein the 2-oxazolin-2-ylamino group is in the 4 position of the indazole nucleus.

12. The compound of claim 11, wherein $R_1$, $R_2$ and $R_3$ are H, H and H.

13. The compound of claim 11, wherein $R_1$, $R_2$ and $R_3$ are 2-$CH_3$, H and H.
14. The compound of claim 11, wherein $R_1$, $R_2$ and $R_3$ are H, Cl and H.
15. The compound of claim 11, wherein $R_1$, $R_2$ and $R_3$ are 1-$CH_3$, Cl and H.
16. The compound of claim 11, wherein $R_1$, $R_2$ and $R_3$ are 2-$CH_3$, Cl and H.
17. The compound of claim 11, wherein $R_1$, $R_2$ and $R_3$ are H, H and 5-$CH_3$.
18. The compound of claim 11, wherein $R_1$, $R_2$ and $R_3$ are 1-$CH_3$, H and 5-$CH_3$.
19. The compound of claim 11, wherein $R_1$, $R_2$ and $R_3$ are 2-$CH_3$, H and 5-$CH_3$.
20. The compound of claim 11, wherein $R_1$, $R_2$ and $R_3$ are H, H and 5-Cl.
21. The compound of claim 11, wherein $R_1$, $R_2$ and $R_3$ are 1-$CH_3$, H and 5-Cl.
22. The compound of claim 11, wherein $R_1$, $R_2$ and $R_3$ are 2-$CH_3$, H and 5-Cl.
23. A compound of claim 4, wherein the 2-oxazolin-2-ylamino group is in the 5 position.
24. The compound of claim 23, wherein $R_1$, $R_2$ and $R_3$ are H, H and H.
25. The compound of claim 23, wherein $R_1$, $R_2$ and $R_3$ are 1-$CH_3$, H and H.
26. The compound of claim 23, wherein $R_1$, $R_2$ and $R_3$ are 2-$CH_3$, H and H.
27. The compound of claim 23, wherein $R_1$, $R_2$ and $R_3$ are H, H and 4-$CH_3$.
28. The compound of claim 23, wherein $R_1$, $R_2$ and $R_3$ are 1-$CH_3$, H and 4-$CH_3$.
29. The compound of claim 23, wherein $R_1$, $R_2$ and $R_3$ are 2-$CH_3$, H and 4-$CH_3$.
30. The compound of claim 23, wherein $R_1$, $R_2$ and $R_3$ are 1-$CH_3$, H and 4-Cl.
31. The compound of claim 23, wherein $R_1$, $R_2$ and $R_3$ are 2-$CH_3$, H and 4-Cl.
32. The compound of claim 23, wherein $R_1$, $R_2$ and $R_3$ are H, H and 6-$CH_3$.
33. The compound of claim 23, wherein $R_1$, $R_2$ and $R_3$ are 1-$CH_3$, H and 6-$CH_3$.
34. The compound of claim 23, wherein $R_1$, $R_2$ and $R_3$ are 2-$CH_3$, H and 6-$CH_3$.
35. The compound of claim 23, wherein $R_1$, $R_2$ and $R_3$ are H, H and 6-Cl.
36. The compound of claim 23, wherein $R_1$, $R_2$ and $R_3$ are 1-$CH_3$, H and 6-Cl.
37. The compound of claim 23, wherein $R_1$, $R_2$ and $R_3$ are 2-$CH_3$, H and 6-Cl.
38. A compound of claim 4, wherein the 2-oxazolin-2-ylamino group is in the 6 position of the indazole nucleus.
39. The compound of claim 38, wherein $R_1$, $R_2$ and $R_3$ are H, H and H.
40. The compound of claim 38, wherein $R_1$, $R_2$ and $R_3$ are 1-$CH_3$, H and H.
41. The compound of claim 38, wherein $R_1$, $R_2$ and $R_3$ are 2-$CH_3$, H and H.
42. The compound of claim 38, wherein $R_1$, $R_2$ and $R_3$ are H, H and 5-$CH_3$.
43. The compound of claim 38, wherein $R_1$, $R_2$ and $R_3$ are 1-$CH_3$, H and 5-$CH_3$.
44. The compound of claim 38, wherein $R_1$, $R_2$ and $R_3$ are 2-$CH_3$, H and 5-$CH_3$.
45. The compound of claim 38, wherein $R_1$, $R_2$ and $R_3$ are H, H and 5-Cl.
46. The compound of claim 38, wherein $R_1$, $R_2$ and $R_3$ are 1-$CH_3$, H and 5-Cl.
47. The compound of claim 38, wherein $R_1$, $R_2$ and $R_3$ are 2-$CH_3$, H and 5-Cl.
48. A compound of claim 4, wherein the 2-oxazolin-2-ylamino group is in the 7 position of the indazole nucleus.
49. The compound of claim 48, wherein $R_1$, $R_2$ and $R_3$ are H, H and H.
50. The compound of claim 48, wherein $R_1$, $R_2$ and $R_3$ are 2-$CH_3$, H and H.
51. The compound of claim 48, wherein $R_1$, $R_2$ and $R_3$ are H, H and 5-$CH_3$.
52. The compound of claim 48, wherein $R_1$, $R_2$ and $R_3$ are H, H and 6-$CH_3$.
53. The compound of claim 48, wherein $R_1$, $R_2$ and $R_3$ are 1-$CH_3$, H and 6-$CH_3$.
54. The compound of claim 48, wherein $R_1$, $R_2$ and $R_3$ are H, H and 6-Cl.
55. The compound of claim 48, wherein $R_1$, $R_2$ and $R_3$ are 1-$CH_3$, H and 6-Cl.
56. The compound of claim 48, wherein $R_1$, $R_2$ and $R_3$ are 2-$CH_3$, H and 6-Cl.
57. A compound of claim 4, which is 1-methyl-7-(2-oxazolin-2-ylamino)-1H-indazole.
58. A compound of claim 5, wherein the 2-thiazolin-2-ylamino group is in the 3 position.
59. The compound of claim 58, wherein $R_1$, $R_3$ and $R_4$ are all hydrogen.
60. A compound of claim 5, wherein the 2-thiazolin-2-ylamino group is in the 4 position.
61. The compound of claim 60, wherein $R_1$, $R_2$ and $R_3$ are respectively H, H and H.
62. The compound of claim 60, wherein $R_1$, $R_2$ and $R_3$ are respectively 1-$CH_3$, H and H.
63. The compound of claim 60, wherein $R_1$, $R_2$ and $R_3$ are respectively 2-$CH_3$, H and H.
64. The compound of claim 60, wherein $R_1$, $R_2$ and $R_3$ are respectively H, Cl and H.
65. The compound of claim 60, wherein $R_1$, $R_2$ and $R_3$ are respectively 1-$CH_3$, Cl and H.
66. The compound of claim 60, wherein $R_1$, $R_2$ and $R_3$ are respectively H, H and 5-$CH_3$.
67. The compound of claim 60, wherein $R_1$, $R_2$ and $R_3$ are respectively 1-$CH_3$, H and 5-$CH_3$.
68. The compound of claim 60, wherein $R_1$, $R_2$ and $R_3$ are respectively 2-$CH_3$, H and 5-$CH_3$.
69. The compound of claim 60, wherein $R_1$, $R_2$ and $R_3$ are respectively H, H and 5-Cl.
70. The compound of claim 60, wherein $R_1$, $R_2$ and $R_3$ are respectively 1-$CH_3$, H and 5-Cl.
71. A compound of claim 5, wherein the 2-thiazolin-2-ylamino group is in the 5 position.
72. The compound of claim 71, wherein $R_1$, $R_2$ and $R_3$ are respectively H, H and H.
73. The compound of claim 71, wherein $R_1$, $R_2$ and $R_3$ are respectively 1-$CH_3$, H and H.
74. The compound of claim 71, wherein $R_1$, $R_2$ and $R_3$ are respectively 2-$CH_3$, H and H.
75. The compound of claim 71, wherein $R_1$, $R_2$ and $R_3$ are respectively H, H and 4-$CH_3$.
76. The compound of claim 71, wherein $R_1$, $R_2$ and $R_3$ are respectively 1-$CH_3$, H and 4-$CH_3$.
77. The compound of claim 71, wherein $R_1$, $R_2$ and $R_3$ are respectively 2-$CH_3$, H and 4-$CH_3$.
78. The compound of claim 71, wherein $R_1$, $R_2$ and $R_3$ are respectively H, H and 4-Cl.

79. The compound of claim 71, wherein $R_1$, $R_2$ and $R_3$ are respectively 1-$CH_3$, H and 4-Cl.

80. The compound of claim 71, wherein $R_1$, $R_2$ and $R_3$ are respectively 2-$CH_3$, H and 4-Cl.

81. The compound of claim 71, wherein $R_1$, $R_2$ and $R_3$ are respectively 1-$CH_3$, H and 6-$CH_3$.

82. The compound of claim 71, wherein $R_1$, $R_2$ and $R_3$ are respectively H, H and 6-Cl.

83. The compound of claim 71, wherein $R_1$, $R_2$ and $R_3$ are respectively 1-$CH_3$, H and 6-Cl.

84. The compound of claim 71, wherein $R_1$, $R_2$ and $R_3$ are respectively 2-$CH_3$, H and 6-Cl.

85. A compound of claim 5, wherein the 2-thiazolin-2-ylamino group is in the 6 position.

86. The compound of claim 85, wherein $R_1$, $R_2$ and $R_3$ are respectively H, H and H.

87. The compound of claim 85, wherein $R_1$, $R_2$ and $R_3$ are respectively 1-$CH_3$, H and H.

88. The compound of claim 85, wherein $R_1$, $R_2$ and $R_3$ are respectively 2-$CH_3$, H and H.

89. The compound of claim 85, wherein $R_1$, $R_2$ and $R_3$ are respectively H, H and 5-$CH_3$.

90. The compound of claim 85, wherein $R_1$, $R_2$ and $R_3$ are respectively 1-$CH_3$, H and 5-$CH_3$.

91. The compound of claim 85, wherein $R_1$, $R_2$ and $R_3$ are respectively 2-$CH_3$, H and 5-$CH_3$.

92. The compound of claim 85, wherein $R_1$, $R_2$ and $R_3$ are respectively H, H and 5-Cl.

93. The compound of claim 85, wherein $R_1$, $R_2$ and $R_3$ are respectively 1-$CH_3$, H and 5-Cl.

94. A compound of claim 5, wherein the 2-thiazolin-2-ylamino group is in the 7 position.

95. The compound of claim 94, wherein $R_1$, $R_2$ and $R_3$ are respectively H, H and H.

96. The compound of claim 94, wherein $R_1$, $R_2$ and $R_3$ are respectively 1-$CH_3$, H and H.

97. The compound of claim 94, wherein $R_1$, $R_2$ and $R_3$ are respectively 2-$CH_3$, H and H.

98. The compound of claim 94, wherein $R_1$, $R_2$ and $R_3$ are respectively 1-$CH_3$, Cl and H.

99. The compound of claim 94, wherein $R_1$, $R_2$ and $R_3$ are respectively H, H and 6-$CH_3$.

100. The compound of claim 94, wherein $R_1$, $R_2$ and $R_3$ are respectively 1-$CH_3$, H and 6-$CH_3$.

101. The compound of claim 94, wherein $R_1$, $R_2$ and $R_3$ are respectively H, H and 6-Cl.

102. The compound of claim 94, wherein $R_1$, $R_2$ and $R_3$ are respectively 1-$CH_3$, H and 6-Cl.

103. The compound of claim 94, wherein $R_1$, $R_2$ and $R_3$ are respectively 2-$CH_3$, H and 6-Cl.

104. The compound of claim 5, which is 6-methyl-5-(2-thiazolin-2-ylamino)-1H-indazole.

105. A compound of claim 4, which is 4-chloro-5-(2-oxazolin-2-ylamino)-1H-indazole.

* * * * *